(12) United States Patent
Koyanagi et al.

(10) Patent No.: US 11,185,298 B2
(45) Date of Patent: Nov. 30, 2021

(54) RADIOGRAPHIC APPARATUS

(71) Applicant: CANON KABUSHIKI KAISHA, Tokyo (JP)

(72) Inventors: Takahiro Koyanagi, Kawasaki (JP); Motoki Tagawa, Chigasaki (JP); Yohei Saito, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 118 days.

(21) Appl. No.: 16/584,664

(22) Filed: Sep. 26, 2019

(65) Prior Publication Data
US 2020/0100740 A1    Apr. 2, 2020

(30) Foreign Application Priority Data

Oct. 1, 2018 (JP) .............................. JP2018-186705

(51) Int. Cl.
*G03B 42/04* (2021.01)
*A61B 6/00* (2006.01)
*G01T 1/20* (2006.01)

(52) U.S. Cl.
CPC ............ *A61B 6/4405* (2013.01); *G03B 42/04* (2013.01); *G01T 1/20* (2013.01)

(58) Field of Classification Search
CPC .. G03B 42/04; G01T 1/20; A61B 6/00; A61B 6/4405; A61B 6/4283; A61B 6/502
See application file for complete search history.

(56) References Cited

U.S. PATENT DOCUMENTS

| | | | |
|---|---|---|---|
| 7,575,374 B2 * | 8/2009 | Watanabe | A61B 6/00 250/370.09 |
| 2010/0183123 A1 * | 7/2010 | Thiery | G03B 42/04 378/187 |
| 2016/0081649 A1 | 3/2016 | Enomoto et al. | |

FOREIGN PATENT DOCUMENTS

| | | |
|---|---|---|
| JP | 2002-082172 A | 3/2002 |
| JP | 2014-171798 A | 9/2014 |
| JP | 2015-051206 A | 3/2015 |
| JP | 2017-29603 A | 2/2017 |
| JP | 2017-067564 A | 4/2017 |
| JP | 2017-198614 A | 11/2017 |

* cited by examiner

*Primary Examiner* — Jurie Yun

(74) *Attorney, Agent, or Firm* — Canon U.S.A., Inc. IP Division

(57) ABSTRACT

A radiographic apparatus includes a radiation detection panel configured to detect radiation, and a housing that covers the radiation detection panel. The housing includes an incident surface receiving the radiation, a side surface adjacent to the incident surface, a rear surface opposing the incident surface, and an inclined surface adjacent to each of the side surface and the rear surface. A recessed handle portion is provided on the inclined surface.

18 Claims, 7 Drawing Sheets

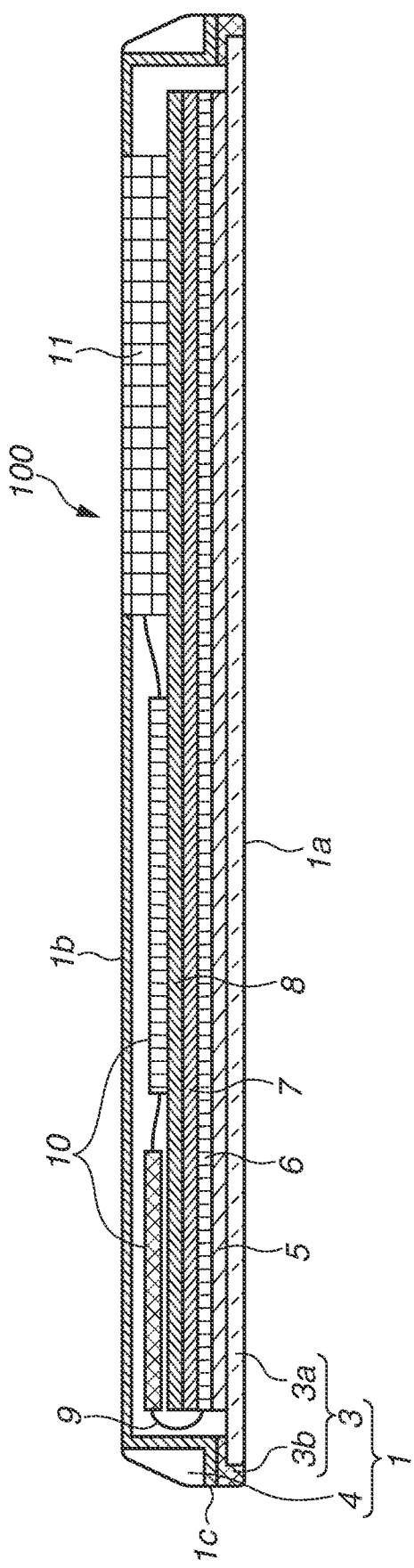

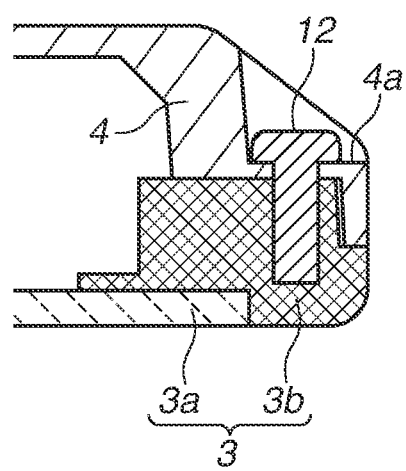
FIG.4A
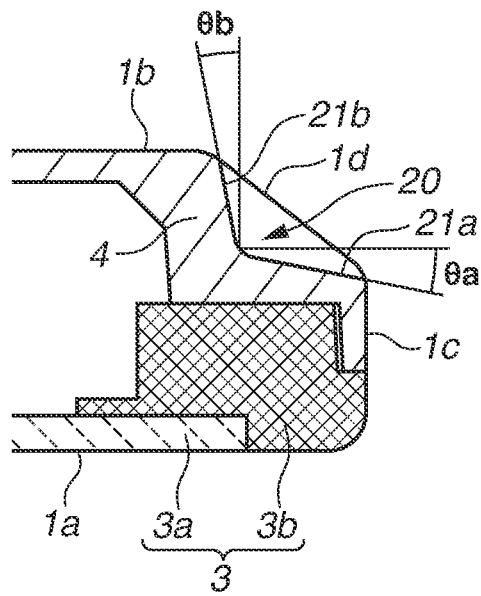
FIG.4B
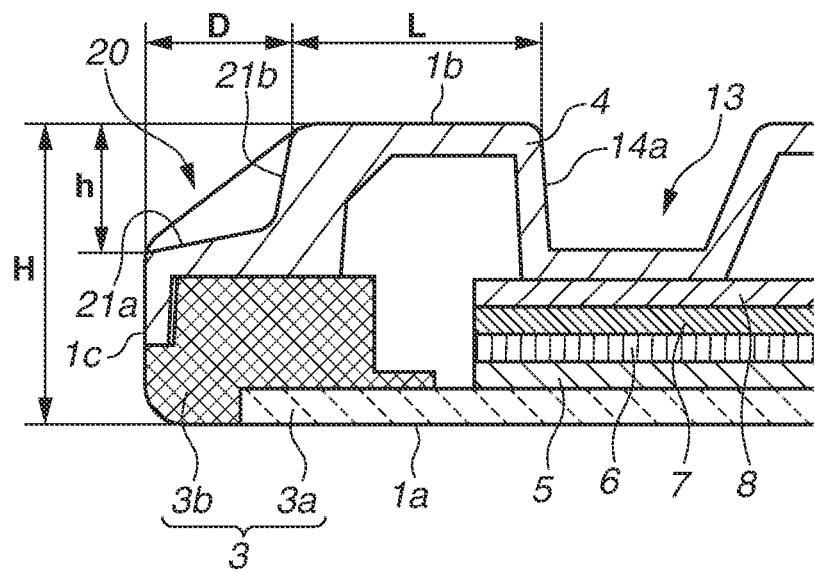
FIG.4C
FIG.4D

FIG.5A
FIG.5B
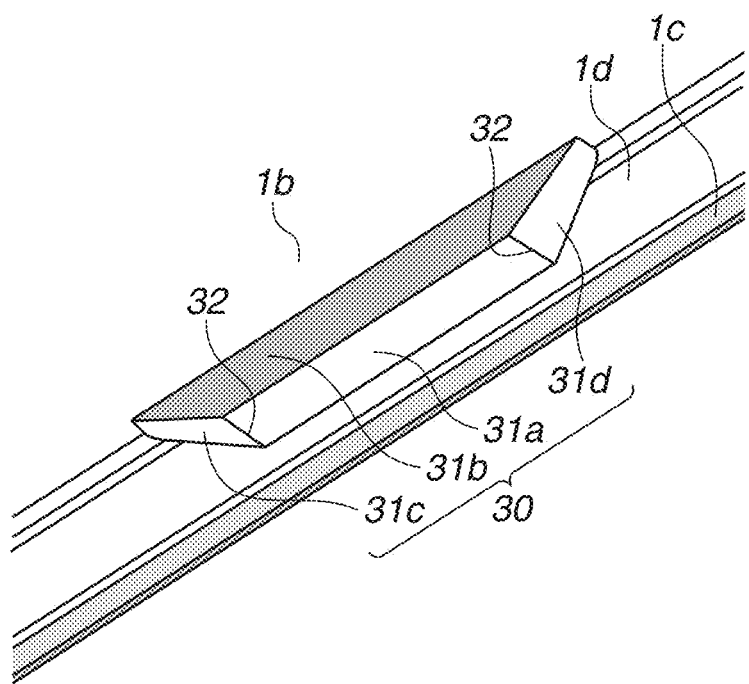
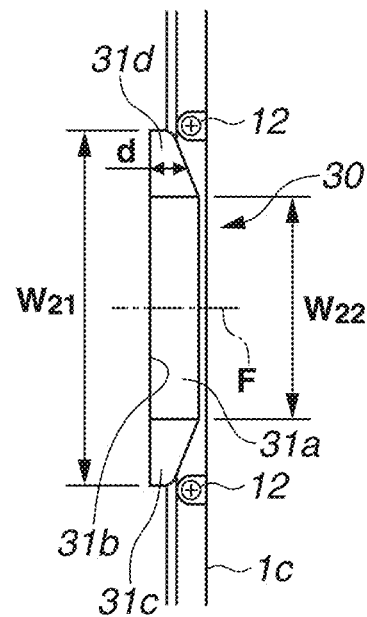

RADIOGRAPHIC APPARATUS

BACKGROUND OF THE INVENTION

Field of the Invention

The present disclosure relates to a radiographic apparatus.

Description of the Related Art

In radiographic imaging for a still image and a moving image in a medical field, a flat panel detector is used. As thickness reduction and weight reduction of a portable radiographic apparatus has advanced, and a wireless radiographic apparatus has been produced.

Japanese Patent Application Laid-Open No. 2002-082172 discusses a radiographic apparatus in which inclined surfaces each inclined in a thickness direction are provided on respective end parts of a bottom surface of a housing body in order to improve portability.

Japanese Patent Application Laid-Open No. 2014-171798 discusses an electronic cassette in which a chamfered part formed as a surface inclined to a side surface and a rear surface of a housing is provided between the side surface and the rear surface for smooth insertion of the cassette into a gap between a patient and an installation surface on which the patient lies.

However, a user may not sufficiently hook the fingers only by providing the inclined surfaces on the bottom surface of the housing body as with the radiographic apparatus discussed in Japanese Patent Application Laid-Open No. 2002-082172.

Further, griping property of the housing by the user may be insufficient only by providing the chamfered part between the side surface and the rear surface of the housing as with the electronic cassette discussed in Japanese Patent Application Laic-Open No. 2014-171798.

SUMMARY OF THE INVENTION

The present disclosure is directed to a radiographic apparatus that can be gripped sufficiently.

According to an aspect of the present disclosure, a radiographic apparatus includes a radiation detection panel configured to detect radiation, and a housing that covers the radiation detection panel, wherein the housing includes an incident surface that receives the radiation, a side surface adjacent to the incident surface, a rear surface opposing the incident surface, and an inclined surface adjacent to each of the side surface and the rear surface, and wherein a recessed handle portion is provided on the inclined surface.

Further features of the present disclosure will become apparent from the following description of exemplary embodiments with reference to the attached drawings.

BRIEF DESCRIPTION OF THE DRAWINGS

FIG. 2 is a cross-sectional view illustrating an entire configuration of the radiographic apparatus.

FIGS. 4A to 4D are cross-sectional views each illustrating a configuration of a part of the radiographic apparatus.

FIGS. 5A and 5B are diagrams each illustrating a configuration of a handle portion according to a second exemplary embodiment.

DESCRIPTION OF THE EMBODIMENTS

Exemplary embodiments of the present disclosure will be described below with reference to the drawings.

Figure 1A:
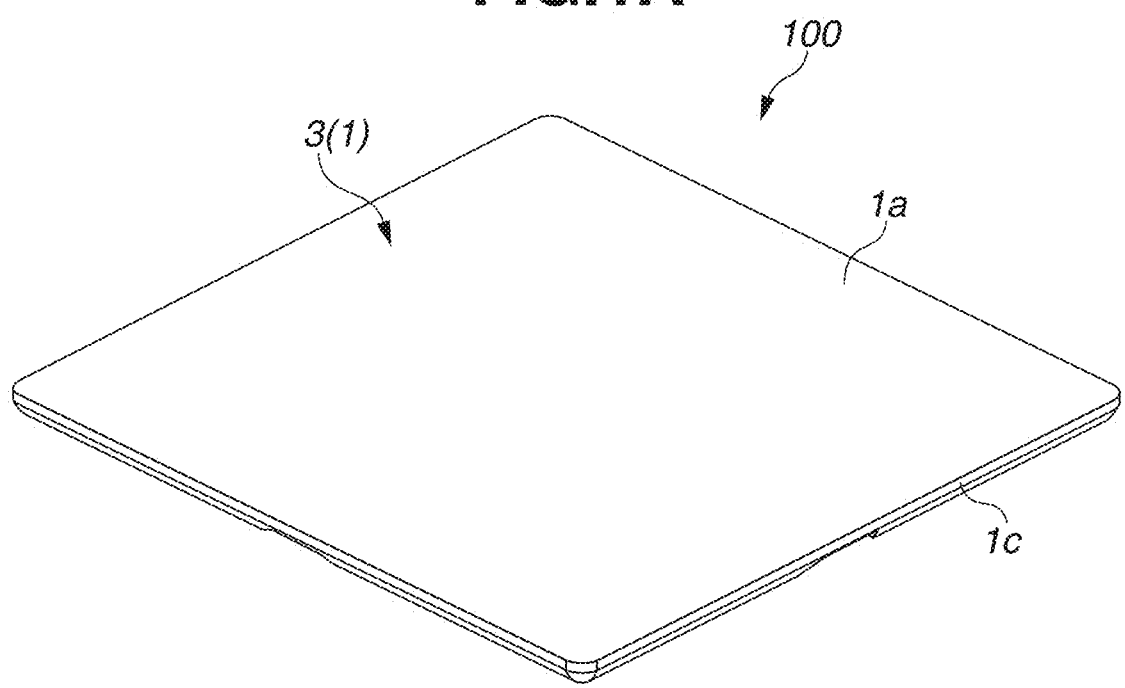
FIGS. 1A and 1B are perspective views each illustrating appearance of a radiographic apparatus according to a first exemplary embodiment.
Figure 1B:
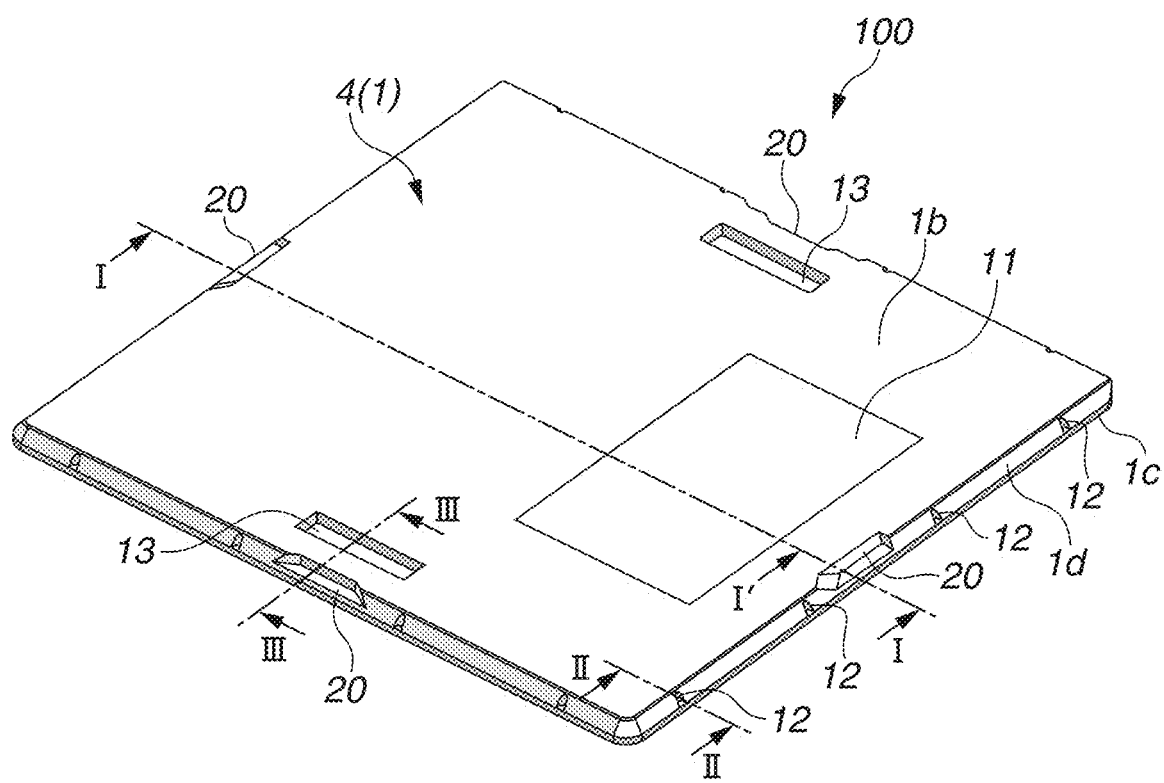

FIG. 1A is a perspective view of a radiographic apparatus 100 viewed from incident surface side, and FIG. 1B is a perspective view illustrating the radiographic apparatus 100 viewed from rear surface side. FIG. 2 is a cross-sectional view taken along a line I-I illustrated in FIG. 1B viewed from an arrow direction.

The radiographic apparatus 100 has a substantially rectangular-parallelepiped shape and an inside thereof is covered with a housing 1.

The housing 1 includes a front surface cover 3 as a first exterior and a rear surface cover 4 as a second exterior. As illustrated in FIG. 2, the front surface cover 3 includes a breast pad 3a and a frame 3b.

The breast pad 3a has a substantially plate shape, and is made of a material having high radiation transmittance. A front surface of the breast pad 3a is a radiation incident surface 1a. The frame 3b is located on a peripheral edge of the breast pad 3a, and is made of a lightweight high-rigidity material such as a magnesium alloy and carbon fiber-reinforced plastic (CFRP), subjected to acrylic coating. A surface of the frame 3b orthogonal to the incident surface 1a is configured as a part of side surfaces 1c of the housing 1. The side surfaces 1c of the frame 3b are adjacent to the incident surface 1a.

The rear surface cover 4 has a substantially plate shape and a peripheral edge thereof is bent toward the front surface cover 3. The rear surface cover 4 is made of a lightweight high-rigidity material such as a magnesium alloy and CFRP, subjected to acrylic coating. A surface of the rear surface cover 4 facing the incident surface 1a is configured as a rear surface 1b. A surface of the rear surface cover 4 orthogonal to the incident surface 1a is configured as a part of the side surfaces 1c of the housing 1. In other words, the side surfaces 1c of the housing 1 according to the present exemplary embodiment are configured of the frame 3b and the rear surface cover 4. However, the surfaces 1c of the housing 1 may be configured of only the frame 3b or only the rear surface cover 4. Further, a surface of the rear surface cover 4 connecting the rear surface 1b and the side surfaces 1c is inclined, and is configured as inclined surfaces 1d. In other words, the inclined surfaces 1d are adjacent to the rear surface 1b and the respective side surfaces 1c.

The front surface cover 3 and the rear surface cover 4 are fastened by a plurality of fastening members 12.

FIG. 4A is a cross-sectional view illustrating a configuration around one fastening member 12 taken along a line II-II illustrated in FIG. 1B viewed from an arrow direction. In FIG. 4A, screws are used as the fastening members 12. The rear surface cover 4 includes counter boring 4a for preventing the respective fastening members 12 from protruding from the housing 1. The fastening members 12 are disposed close to an outer edge of the housing 1 in order to secure a wide internal space of the housing 1. A seal member to secure waterproofness may be provided between the front surface cover 3 and the rear surface cover 4.

Further, as the other components, an external connection terminal unit for receiving power from an external apparatus and performing data communication, an antenna unit, a user interface (IF) unit on which a power switch and a status display unit are mounted are disposed on the housing 1.

As illustrated in FIG. 2, an impact absorbing sheet 5, a radiation detection panel 6, a radiation shielding sheet 7, and a holding base 8 are disposed inside the housing 1 so as to be overlapped in order from the incident surface 1a.

The impact absorbing sheet 5 protects the radiation detection panel 6 from an impact applied from outside.

The radiation detection panel 6 detects radiation and converts the radiation into an image signal. The radiation detection panel 6 is an imaging detection panel in which a plurality of conversion elements for converting a dosage of radiation into a charge amount and a plurality of pixel devices each including a switch element for transferring an electric signal are two-dimensionally arranged on an insulating substrate (e.g., glass substrate). The radiation detection panel 6 includes a scintillator that converts the radiation into the image signal. Further, the radiation detection panel 6 is connected to a readout circuit, a control substrate 10 through a flexible circuit board 9. The readout circuit reads out the electric signals from the pixel devices of the radiation detection panel 6. The control substrate 10 performs, for example, electric signal control of a drive circuit and a direct-current voltage conversion to supply, to the switch elements, a driving signal having a voltage to make the switch elements conductive.

The case where the radiation detection panel 6 is of an indirect conversion type has been described above. However, the type of the radiation detection panel 6 is not limited thereto. For example, the radiation detection panel 6 may be of a direct conversion type including a conversion element unit in which conversion elements each made of amorphous selenium (a-Se) and electric elements such as thin-film transistors (TFTs) are two-dimensionally arranged.

The radiation shielding sheet 7 is made of a material shielding a radiation, for example, a material containing a heavy metal of any of lead (Pb), barium (Ba), tantalum (Ta), molybdenum (Mo), and tungsten (W), or stainless steel.

The holding base 8 holds the components configuring the radiographic apparatus 100. The control substrate 10, a secondary battery 11, a wireless module unit (not illustrated), etc. are disposed on the rear surface 1b side of the holding base 8. The secondary battery 11 supplies driving power. The wireless module unit functions as a wireless transmission unit that wirelessly transmits the image signal to the external apparatus, and as a wireless reception unit.

The radiographic apparatus 100 having the above-described configuration detects radiation that has passed through a subject and converts the detected radiation into the image signal by the radiation detection panel 6, and then transfers the image signal to the external apparatus. The external apparatus displays the transferred image signal on a monitor for use of diagnosis and the like.

The housing 1 according to the present exemplary embodiment includes recessed handle portions 20 on the respective inclined surfaces 1d in order to improve griping property by the user. The handle portions 20 each have a shape recessed toward the inside of the housing 1 from the respective inclined surfaces 1d. Providing the handle portions 20 in the above-described manner makes it possible to improve the griping property and portability of the radiographic apparatus 100 by the user. This facilitates lifting and handling the radiographic apparatus 100 to enable quick imaging.

As illustrated in FIG. 1B, the housing 1 according to the present exemplary embodiment includes four side surfaces 1c, and includes the inclined surface 1d between each of the side surfaces 1c and the rear surface 1b. Accordingly, the housing 1 includes four inclined surfaces 1d adjacent to the respective side surfaces 1c. In the housing 1 according to the present exemplary embodiment, one handle portion 20 is provided on each of the four inclined surfaces 1d. In other words, when the housing 1 has a rectangular shape including four sides, one handle portion 20 is provided on each of the four sides. Providing the handle portion 20 on each of the four sides of the housing 1 as described above enables the user to handle the radiographic apparatus 100 from all directions. Each of the handle portions 20 is located at a substantially center of a length of each side, and is located between the two fastening members 12.

The housing 1 according to the present exemplary embodiment further includes recessed griping portions 13 on the rear surface 1b. Providing the griping portions 13 as described above enables the user to firmly grip the radiographic apparatus 100, and the user can easily carry the radiographic apparatus 100, for example, with one hand.

As illustrated in FIG. 1B, in the housing 1 according to the present exemplary embodiment, each of the griping portions 13 is provided at a position close to the handle portion 20, on the rear surface 1b. More specifically, in a back view, each of the griping portions 13 is located on a straight line orthogonal to the side provided with the handle portion 20. In the present exemplary embodiment, two griping portions 13 are separately provided between the handle portions 20 provided on two opposing sides. The griping portions 13 each have a substantially rectangular shape elongated along the closest side in the back view.

Next, a specific shape of each of the handle portions 20 is described with reference to FIGS. 3A and 3B and FIGS. 4A to 4D.

Figure 3A:
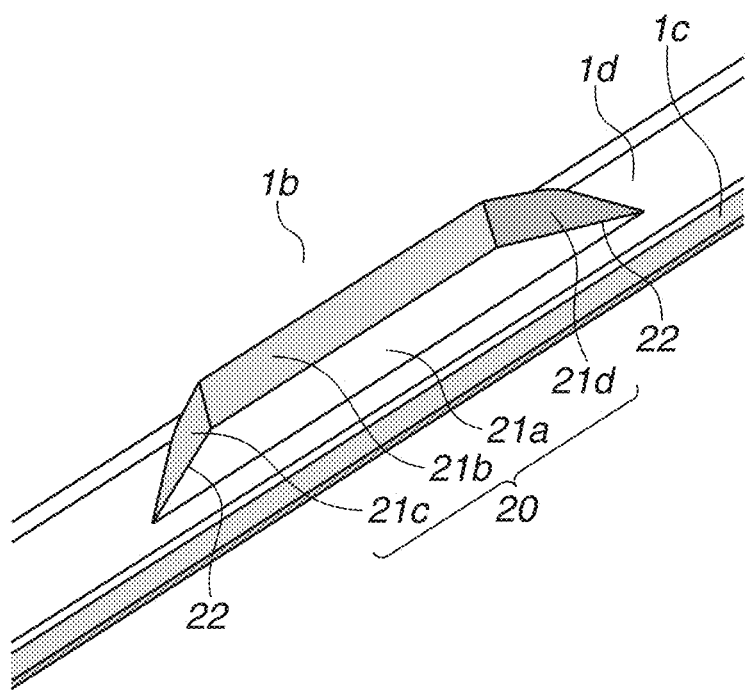
FIGS. 3A and 3B are diagrams each illustrating a configuration of a handle portion.
Figure 3B:
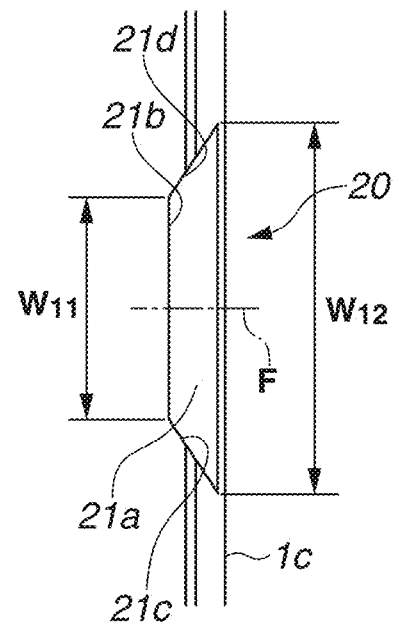

FIG. 3A is a partial perspective view illustrating one handle portion 20, and FIG. 3B is a back view illustrating the handle portion 20.

As illustrated in FIG. 3A, the handle portion 20 includes a bottom wall 21a, an inner wall 21b, a first side wall 21c, and a second side wall 21d. A surface of the bottom wall 21a is an example of a handle surface, and a surface of the inner wall 21b is an example of an inner wall surface. A surface of the first side wall 21c and a surface of the second side wall 21d are an example of a first side-wall surface and an example of a second side-wall surface, respectively. The first side-wall surface and the second side-wall surface according to the present exemplary embodiment are orthogonal to the incident surface 1a and the rear surface 1b.

The bottom wall 21a is adjacent to the corresponding side surface 1c of the housing 1. The bottom wall 21a has a substantially quadrangle shape (substantially trapezoidal shape) in the back view. Each of the first side wall 21c and the second side wall 21d is adjacent to the bottom wall 21a through a side 22 that extends from the side surface 1c toward the housing 1, out of sides forming the substantially quadrangle shape of the bottom wall 21a. The inner wall 21b is adjacent to the bottom wall 21a, the first side wall 21c, and the second side wall 21d.

As illustrated in FIG. 3B, the first side wall 21c and the second side wall 21d are inclined in a direction in which a distance between the first side wall 21c and the second side wall 21d is increased as the first side wall 21c and the second side wall 21d come closer to the side surface 1c from the inner wall 21b. In other words, a width $W_{11}$ of the bottom wall 21a on the inner wall 21b side and a width $W_{12}$ of the bottom wall 21a on the side surface 1c side satisfy relationship of $W_{11} \leq W_{12}$.

Assuming that a distal joint width of a finger joint is about 20 mm per one finger, the widths are preferably set to $W_{11} \geq 40$ mm and $W_{12} \geq 60$ mm in order to enable the user to hook two to three fingers to the bottom wall 21a. The user can hook the fingers to the bottom wall 21a by moving the fingers from the incident surface 1a along the side surface 1c and the inclined surface 1d. Further, the user can smoothly hook the fingers to the handle portion 20 by moving the fingers along the side surface 1c and the inclined surface 1d of the housing 1. As described above, the user can easily hook the fingers to the handle portion 20 without directly viewing the handle portion 20.

Further, the handle portion 20 has a substantially symmetric shape with respect to a virtual plane F that is located at a midpoint between the first side wall 21c and the second side wall 21d.

FIG. 4B is a cross-sectional view taken along a line I-I' of FIG. 1B. FIG. 4C is a cross-sectional view taken along a line III-III of FIG. 1B.

As illustrated in FIG. 4B, the bottom wall 21a of the handle portion 20 is not parallel to but inclined to the incident surface 1a and the rear surface 1b. More specifically, the bottom wall 21a is inclined in a direction approaching the incident surface 1a as the bottom wall 21a comes closer to the side surface 1c. As illustrated in FIG. 4B, an inclination angle of the bottom wall 21a to the incident surface 1a is θa.

Further, the inner wall 21b of the handle portion 20 is not parallel to the side surface 1c, or is not orthogonal to but inclined to the incident surface 1a and the rear surface 1b. More specifically, the inner wall 21b is inclined in a direction apart from the side surface 1c as the inner wall 21b comes closer to the rear surface 1b. As illustrated in FIG. 4B, an inclination angle of the inner wall 21b to the side surface 1c, or an inclination angle of the inner wall 21b to a vertical direction orthogonal to the incident surface 1a is θb.

Although the inclination angles θa and θb are each set to about 10 degrees in the present exemplary embodiment, the angles θa and θb are not limited thereto as long as an angle gradient difference with respect to the inclined surface 1d of the housing 1 is secured to be 15 degrees or more. As described above, inclining the bottom wall 21a and the inner wall 21b makes it possible to suppress cross-sectional area reduction of the rear surface cover 4 of the housing 1 caused by the handle portion 20 to maintain rigidity while securing a height of an entrance of the handle portion 20.

Further, a boundary between the bottom wall 21a and the inner wall 21b is continuously connected by a curved surface. Therefore, when the user hooks the fingers to the handle portion 20, the user can easily touch the boundary curved surface between the bottom wall 21a and the inner wall 21b, which increases a contact area between the handle portion 20 and the fingers.

The height of the handle portion 20 is described with reference to FIG. 4C.

The handle portion 20 preferably has the height that enables the user to easily hook the fingers to the handle portion 20 when the radiographic apparatus 100 is placed on a flat plate such as an imaging base with the rear surface 1b down. A thickness H of the radiographic apparatus 100 is defined as a distance between the incident surface 1a and the rear surface 1b. Further, a height h of the handle portion 20 is defined as a distance between the position of the bottom wall 21a on the side surface 1c side and the rear surface 1b. In this case, the height h of the handle portion 20 preferably satisfies relationship of h≥H/3 or h≥5 mm. In other words, the height h of the handle portion 20 is preferably ⅓ or more of the thickness H of the radiographic apparatus 100 (lower than thickness H), or equal to or larger than 5 mm (lower than thickness H). Further, the height h of the handle portion 20 more preferably satisfies relationship of h≥H/3 and h≥5 mm. Furthermore, the height h of the handle portion 20 is desirably ⅓ or more and ⅔ or less of the thickness H of the radiographic apparatus 100, or 5 mm or more and 10 mm or less. In the present exemplary embodiment, the thickness H of the housing 1 is equivalent to a standard dimension of a general imaging cassette specified by JIS Z4905.

In a case where a boundary between the bottom wall 21a and the side surface 1c is continuously connected by a curved surface as illustrated in FIG. 4D, an intersection P of a line extended from the bottom wall 21a on the side surface 1c side and a line extended from the side surface 1c on the rear surface 1b side can be used as a reference position for measurement of the height h of the handle portion 20.

As illustrated in FIG. 4C, the griping portion 13 is located at a position where a distance L from the handle portion 20 becomes lower than or equal to 30 mm. In other words, the distance L is preferably lower than or equal to a length from a fingertip to a distal interphalangeal joint (first joint). Accordingly, the user can grip the griping portion 13 through a series of operations to move the fingers from the handle portion 20 to the griping portion 13, which allows improving the handling property by the user.

In a case where a boundary between the inner wall 21b and the rear surface 1b is continuously connected by a curved surface, an intersection of a line extended from the inner wall 21b on the rear surface 1b side and a line extended from the rear surface 1b on the side surface 1c side can be used as a reference position for measurement of the distance L, in a manner similar to FIG. 4D. In a case where a boundary between a side wall 14a of the griping portion 13 and the rear surface 1b is continuously connected by a curved surface, an intersection of a line extended from the side wall 14a of the griping portion 13 to the rear surface 1b side and a line extended from the rear surface 1b on the griping portion 13 side can be used as a reference position for measurement of the distance L, in a manner similar to FIG. 4D.

As described above, according to the present exemplary embodiment, since the recessed handle portion 20 is provided on the inclined surface 1d of the housing 1, the user can hook the fingers to the handle portion 20, which allows improving the griping property of the radiographic apparatus 100.

Further, according to the present exemplary embodiment, the handle portion 20 includes the handle surface (bottom wall 21a) adjacent to the side surface 1c, and the handle surface is inclined in a direction approaching the incident surface 1a as the handle surface comes closer to the side surface 1c. This makes it possible to suppress cross-sectional area reduction caused by the handle portion 20, and to maintain rigidity. The handle surface may be inclined in a direction apart from the incident surface 1a as the handle surface comes closer to the side surface 1c, or may be parallel to the incident surface 1a. In the case where the handle surface is inclined in the direction apart from the incident surface 1a as the handle surface comes closer to the side surface 1c, the user can deeply hook the fingers to the handle portion 20, which makes it possible to further improve griping property of the radiographic apparatus 100.

Next, a handle portion 30 according to a second exemplary embodiment is described. Components similar to those according to the first exemplary embodiment are denoted by the same reference numerals and description thereof is appropriately omitted.

FIG. 5A is a partial perspective view illustrating the handle portion 30, and FIG. 5B is a back view illustrating the handle portion 30.

As illustrated in FIG. 5A, the handle portion 30 includes a bottom wall 31a, an inner wall 31b, a first side wall 31c, and a second side wall 31d. A surface of the bottom wall 31a is an example of the handle surface, and a surface of the inner wall 31b is an example of the inner wall surface. A surface of the first side wall 31c and a surface of the second side wall 31d are an example of the first side-wall surface and an example of the second side-wall surface, respectively. The first side-wall surface and the second side-wall surface according to the present exemplary embodiment are inclined to the incident surface 1a and the rear surface 1b.

The bottom wall 31a is adjacent to the corresponding side surface 1c of the housing 1. The bottom wall 31a has a substantially quadrangle shape (substantially rectangular shape) in the back view. Each of the first side wall 31c and the second side wall 31d is adjacent to the bottom wall 31a through a side 32 that extends from the side surface 1c toward the housing 1, out of sides forming the substantially quadrangle shape of the bottom wall 31a. The inner wall 31b is adjacent to the bottom wall 31a, the first side wall 31c, and the second side wall 31d.

As illustrated in FIG. 5B, the first side wall 31c and the second side wall 31d are inclined in a direction in which a distance between the first side wall 31c and the second side wall 31d is increased as the first side wall 31c and the second side wall 31d come closer to the rear surface 1b from the bottom wall 31a. In other words, a width $W_{22}$ of the bottom wall 31a and a width $W_{21}$ of the inner wall 31b on the rear surface 1b side satisfy relationship of $W_{21} \geq W_{22}$.

Further, in the back view, a distance d between a boundary position with the inclined surface 1d and the inner wall 31b in each of the first side wall 31c and the second side wall 31d is reduced toward the inner wall 31b side as each of the first side wall 31c and the second side wall 31d comes closer to the rear surface 1b. In contrast, an area of the inclined surface 1d adjacent to the first side wall 31c and the second side wall 31d is increased. Accordingly, the fastening members 12 can be disposed at positions close to the handle portion 30. In FIG. 5B, the fastening members 12 are arranged over the width $W_{21}$ of the inner wall 31b. Therefore, in a case where the width of the handle portion 20 and the width of the handle portion 30 are equal to each other, the handle portion 30 can reduce the distance between the fastening members 12 as compared with the first exemplary embodiment, which makes it possible to improve rigidity of the housing 1. Arrangement of the fastening members 12 is not limited to the arrangement over the width $W_{21}$ of the inner wall 31b, and the fastening members 12 may be disposed inside the width $W_{21}$ of the inner wall 31b.

Further, the surface of the bottom wall 31a of the handle portion 30 is subjected to treatment that makes a friction coefficient of the surface of the bottom wall 31a larger than a friction coefficient of a surface of each of the side surface 1c and the inclined surface 1d. More specifically, the surface of the bottom wall 31a is partially coated with a rubber having a large friction coefficient or bonded with a sheet of the different material. Accordingly, when the user hooks the fingers to the handle portion 30 and lifts up the radiographic apparatus, it is possible to reduce possibility of sliding-down. In addition to the surface of the bottom wall 31a of the handle portion 30, the inner wall 31b, the first side wall 31c, and the second side wall 31d may be similarly subjected to the treatment that makes the friction coefficient larger than the friction coefficient of the surface of each of the side surface 1c and the inclined surface 1d.

As described above, according to the present exemplary embodiment, since the first side wall 31c and the second side wall 31d are inclined in the direction in which the distance between the first side wall 31c and the second side wall 31d is increased as the first side wall 31c and the second side wall 31d come to closer to the rear surface 1b, it is possible to reduce the distance between the fastening members 12 when the handle portion 30 is disposed between the fastening members 12. This makes it possible to improve rigidity of the housing 1.

In the above-described first and second exemplary embodiments, the cases where the first side walls 21c and 31c and the second side walls 21d and 31 are inclined in specific directions have been described. However, the configuration is not limited to these cases. For example, the walls may be inclined so as to increase a projection area of each of the handle portions 20 and 30 when the housing 1 is viewed from the rear surface 1b, in order to achieve the effect facilitating hooking of the fingers.

Next, radiographic apparatuses 200 to 500 according to a third exemplary embodiment are described. Components similar to those according to the first exemplary embodiment or the second exemplary embodiment are denoted by the same reference numerals, and description thereof is appropriately omitted.

FIGS. 6A to 6D are back views respectively illustrating configurations of the radiographic apparatuses 200 to 500. In the radiographic apparatuses 200 to 500 respectively illustrated in FIGS. 6A to 6D, a handle portion is provided on each of four sides of the housing 1.

Figure 6A:
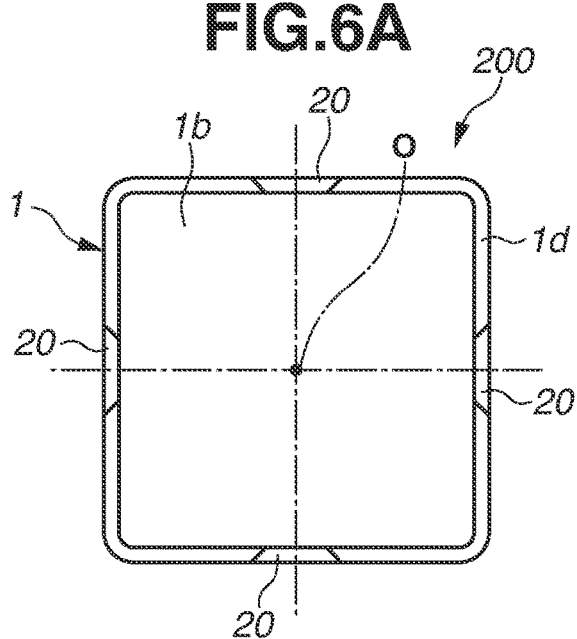
FIGS. 6A to 6D are plan views each illustrating a rear surface of a radiographic apparatus according to a third exemplary embodiment.

In the radiographic apparatus 200 illustrated in FIG. 6A, the handle portions 20 each having an equivalent shape are provided on respective four sides of the housing 1. A point O indicates a center position of the housing 1. Each of the handle portions 20 is disposed on a substantially center of a length of each side. In such a configuration of the radiographic apparatus 200, even in a case where the user hooks fingers to the handle portions 20, it is difficult for the user to recognize whether the radiographic apparatus 200 is directed in a longitudinal direction or a lateral direction.

Figure 6B:
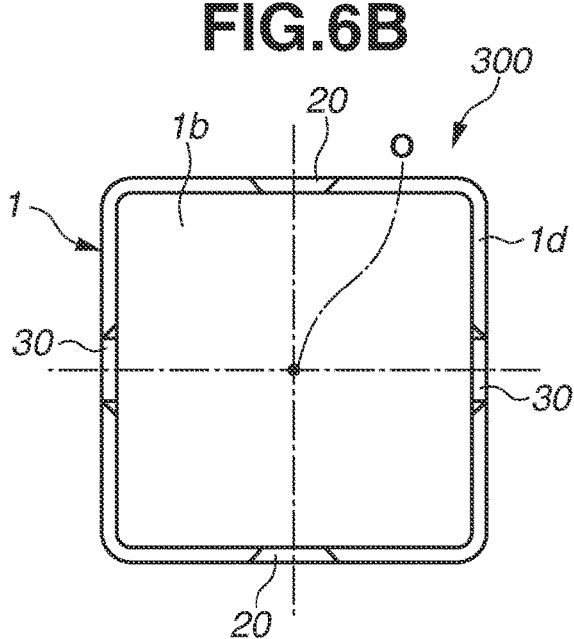

In the radiographic apparatus 300 illustrated in FIG. 6B, the handle portions 20 each having the equivalent shape are provided on opposing sides, and the handle portions 30 each having the equivalent shape different from the shape of the handle portion 20 are provided on the other opposing sides, out of the four sides of the housing 1, and the handle portions 20 and 30 having the different shapes are provided on the adjacent sides. Therefore, when the user hooks the fingers to the handle portions 20, the user can recognize that the user touches which of the handle portions 20 and the handle portions 30, from touch feeling because of the different shapes. Accordingly, the user can recognize whether the radiographic apparatus 300 is directed in the longitudinal direction or the lateral direction without directly viewing the radiographic apparatus 300. In the present exemplary embodiment, the handle portion 20 according to the first exemplary embodiment is used. However, a handle portion having a different shape therefrom may be used. In addition, the handle portion 30 according to the second exemplary embodiment is used. However, a handle portion having a different shape therefrom may be used.

Figure 6C:
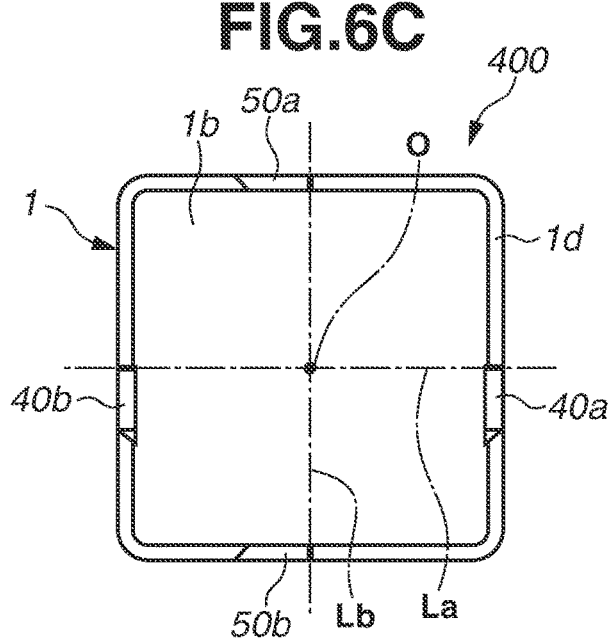

In the radiographic apparatus 400 illustrated in FIG. 6C, handle portions 40a, 40b, 50a, and 50b are provided on the respective four sides of the housing 1. Shapes of the handle portions 40a, 40b, 50a, and 50b are different from one another. However, the shape of the handle portion 40a and the shape of the handle portion 40b are substantially symmetric with respect to a straight line Lb. The straight line Lb is parallel to the side provided with the handle portion 40a or the side provided with the handle portion 40b, and passes through the point O. Further, the shape of the handle portion 50a and the shape of the handle portion 50b are substantially symmetric with respect to a straight line La. The straight line La is parallel to the side provided with the handle portion 50a or the side provided with the handle portion 50b, and passes through the point O.

Figure 7:
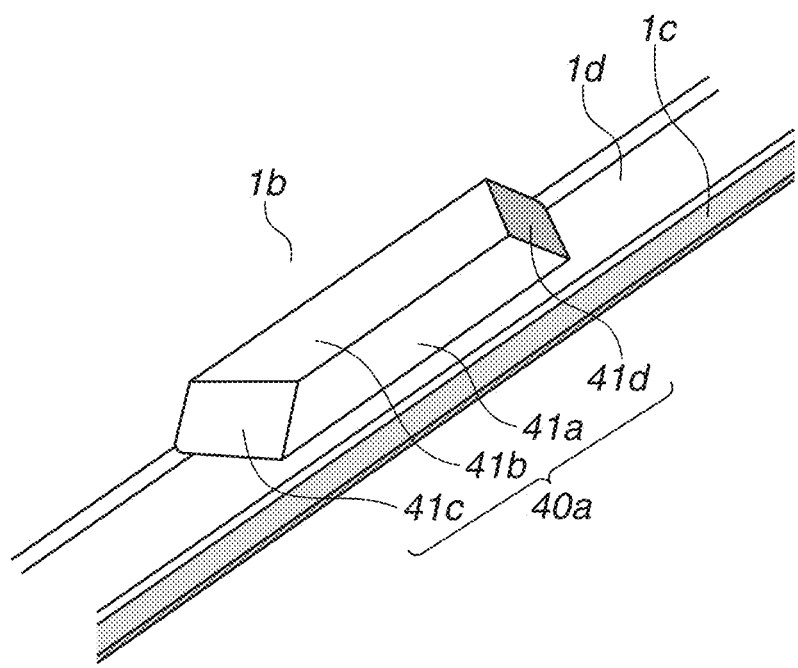
FIG. 7 is a perspective view illustrating a configuration of a handle portion.

FIG. 7 is a partial perspective view illustrating the handle portion 40a. Components similar to those according to the first exemplary embodiment are denoted by the same reference numerals, and description thereof is appropriately omitted.

As illustrated in FIG. 7, the handle portion 40a includes a bottom wall 41a, an inner wall 41b, a first side wall 41c, and a second side wall 41d. The first side wall 41c and the second side wall 41d have shapes different from each other. The first side wall 41c is not parallel to but inclined to the incident surface 1a and the rear surface 1b. On the other hand, the second side wall 41d is orthogonal to each of the incident surface 1a and the side surface 1c. Therefore, the first side wall 41c and the second side wall 41d are different in angle at least to the side surface 1c from each other. In other words, the shape of the first side wall 41c and the shape of the second side wall 41d are asymmetric with respect to a virtual plane F that is located at a midpoint between the first side wall 41c and the second side wall 41d.

Further, also in each of the handle portions 40b, 50a, and 50b, one of the first side wall and the second side wall is orthogonal to the incident surface 1a and the corresponding side surface 1c.

When the user hooks the fingers to the handle portion 40a, the user can recognize difference of the shapes of the side walls from touch feeling. Therefore, the user can recognize the orientation (which orientation in longitudinal direction, or which orientation in lateral direction) of the radiographic apparatus 400 without directly viewing the radiographic apparatus 400.

Further, as illustrated in FIG. 6C, the side wall orthogonal to the incident surface 1a and the corresponding side surface 1c is disposed on the straight line La or the straight line Lb (substantially on straight line). Therefore, even when the radiographic apparatus 400 is placed just below the subject in supine imaging, the user can confirm the center position of the radiographic apparatus 400 by the fingers, which makes it possible to improve work efficiency in the imaging.

Further, as illustrated in FIG. 6C, making the shapes of the adjacent handle portions out of the handle portions 40a, 40b, 50a, and 50b different from each other enables the user to recognize whether the radiographic apparatus 400 is directed in the longitudinal direction or the lateral direction without directly viewing the radiographic apparatus 400.

Figure 6D:
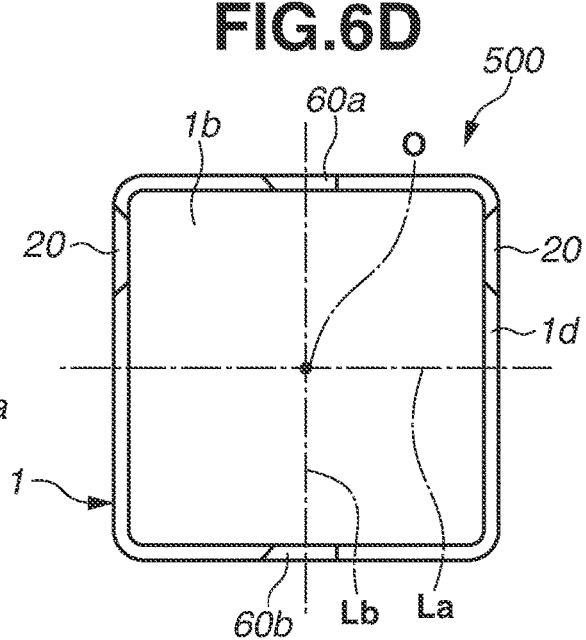

In the radiographic apparatus 500 illustrated in FIG. 6D, handle portions 20, 60a, and 60b are provided on the four sides of the housing 1. The handle portions 20, 60a, and 60b have different shapes. The shape of the handle portion 60a and the shape of the handle portion 60b are substantially symmetric with respect to the straight line La.

The handle portions 20 located on the opposing sides are not disposed on the straight line La but disposed on positions (ends) deviated to the handle portion 60a side. Therefore, when the user hooks the fingers to the handle portions 20, the user can recognize the positions of the handle portions 20. Therefore, the user can recognize the orientation (which orientation in longitudinal direction, or which orientation in lateral direction) of the radiographic apparatus 500, without directly viewing the radiographic apparatus 500.

As described above, according to the present exemplary embodiment, the user can recognize the orientation of the radiographic apparatus and the longitudinal or lateral direction through combination of the shapes and arrangement of the handle portions, which makes it possible to further improve handling efficiency of the radiographic apparatus.

In addition, according to the present exemplary embodiment, the first inclined surface 1d and the second inclined surface 1d adjacent to each other are provided on adjacent different two side surfaces 1c, and the shape of the first handle portion 20 provided on the first inclined surface 1d and the shape of the second handle portion 30 provided on the second inclined surface 1d are different from each other. Therefore, the user can recognize whether the radiographic apparatus is directed in the longitudinal direction or the lateral direction by touching the first handle portion 20 or the second handle portion 30.

Further, one of the first side wall and the second side wall is disposed on the substantially straight line (straight line La or Lb) that passes through the center position (point O) of the radiographic apparatus and is orthogonal to the corresponding side surface 1c. Therefore, the user can recognize the center position of the radiographic apparatus by touching one of the first side wall and the second side wall.

Although the exemplary embodiments of the present disclosure have been described above, the present disclosure is not limited to those exemplary embodiments, and various modifications and alternations can be made within the scope of the present disclosure. Further, the above-described exemplary embodiments may be appropriately combined.

In the above-described exemplary embodiments, the case where one handle portion is provided on one inclined surface 1d has been described. However, a plurality of handle portions may be provided on one inclined surface 1d.

In the above-described exemplary embodiments, the case where the housing 1 includes the four inclined surfaces 1d adjacent to the respective side surfaces 1c has been described. However, the housing 1 may include one to three inclined surfaces 1d. For example, in a case where the housing 1 includes one inclined surface 1d, the handle portion is provided only on the one inclined surface 1d, and the inclined surface 1d is not adjacent to the side surface 1c opposing the side surface 1c provided with the handle portion.

The exemplary embodiments can improve griping property of the radiographic apparatus.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-186705, filed Oct. 1, 2018, which is hereby incorporated by reference herein in its entirety.

What is claimed is:

1. A radiographic apparatus, comprising:
a radiation detection panel configured to detect radiation;

a battery configured to supply power to the radiation detection panel; and a housing that covers the radiation detection panel, wherein the housing includes an incident surface that receives the radiation, a side surface adjacent to the incident surface, a rear surface opposing the incident surface, and an inclined surface adjacent to each of the side surface and the rear surface, wherein the battery is arranged behind the radiation detection panel at the rear surface side, and wherein a recessed handle portion is provided on the inclined surface.

2. The radiographic apparatus according to claim 1, wherein the handle portion includes a handle surface adjacent to the side surface, and wherein the handle surface is inclined to the incident surface.

3. The radiographic apparatus according to claim 2, wherein the handle surface is inclined in a direction approaching the incident surface as the handle surface comes closer to the side surface.

4. The radiographic apparatus according to claim 2, wherein a distance between the handle surface and the rear surface is ⅓ or more of a distance between the incident surface and the rear surface, or 5 mm or more.

5. The radiographic apparatus according to claim 2, wherein the handle surface has a substantially quadrangle shape as viewed from a direction orthogonal to the rear surface, and wherein the handle portion includes a first side-wall surface and a second side-wall surface that are adjacent to the handle surface through two sides extending from the side surface toward the housing out of sides forming the substantially quadrangle shape of the handle surface, and an inner wall surface that is adjacent to the handle surface, the first side-wall surface, and the second side-wall surface.

6. The radiographic apparatus according to claim 5, wherein at least one of the first side-wall surface and the second side-wall surface is inclined in a direction in which a distance between the first side-wall surface and the second side-wall surface is increased as at least one of the first side-wall surface and the second side-wall surface comes closer to the side surface.

7. The radiographic apparatus according to claim 6, wherein the first side-wall surface and the second side-wall surface are asymmetric with respect to a virtual plane that is located at a midpoint between the first side-wall surface and the second side-wall surface.

8. The radiographic apparatus according to claim 5, wherein at least one of the first side-wall surface and the second side-wall surface is inclined in a direction in which a distance between the first side-wall surface and the second side-wall surface is increased as at least one of the first side-wall surface and the second side-wall surface comes closer to the rear surface.

9. The radiographic apparatus according to claim 5, wherein one of the first side-wall surface and the second side-wall surface is disposed on a substantially straight line that passes through a center position of the radiographic apparatus and is orthogonal to the side surface, in a back view.

10. The radiographic apparatus according to claim 1, wherein the handle portion includes an inner wall surface adjacent to the rear surface, and wherein the inner wall surface is inclined to the side surface.

11. The radiographic apparatus according to claim 10, wherein the inner wall surface is inclined in a direction apart from the side surface as the inner wall surface comes closer to the rear surface.

12. The radiographic apparatus according to claim 1, wherein the handle portion is larger in friction coefficient than the inclined surface.

13. The radiographic apparatus according to claim 1, wherein the housing includes a first inclined surface and a second inclined surface that are adjacent to respective different two side surfaces adjacent to each other, and wherein a shape of a first handle portion provided on the first inclined surface and a shape of a second handle portion provided on the second inclined surface are different from each other.

14. The radiographic apparatus according to claim 1, wherein the housing has a rectangular shape and includes four side surfaces adjacent to the incident surface, and wherein the handle portion is provided on an inclined surface adjacent to a side surface opposing a side surface not provided with an inclined surface, out of the four side surfaces.

15. The radiographic apparatus according to claim 1, wherein the housing includes a first exterior including the incident surface, and a second exterior including the rear surface, and wherein the handle portion is located between two fastening members fastening the first exterior and the second exterior.

16. The radiographic apparatus according to claim 1, wherein a recessed griping portion is provided on the rear surface, and wherein the griping portion and the handle portion are disposed on a straight line orthogonal to the side surface provided with the handle portion.

17. The radiographic apparatus according to claim 1, wherein a recessed griping portion is provided on a peripheral area of the rear surface, and wherein the griping portion and the handle portion are disposed at respective positions across a boundary between the side surface and the inclined surface.

18. The radiographic apparatus according to claim 1, wherein the housing has a rectangular shape and includes four side surfaces adjacent to the incident surface, and wherein the handle portion is provided on an inclined surface adjacent to a side surface that is most adjacent to the battery.

\* \* \* \* \*